(12) United States Patent
Simon et al.

(10) Patent No.: US 7,023,552 B2
(45) Date of Patent: Apr. 4, 2006

(54) PROCESS FOR MAKING A COLORED MAKE-UP COSMETIC COMPOSITION WITH CONTROLLED TRANSMITTANCE

(75) Inventors: Jean-Christophe Simon, Paris (FR); Nathalie Jager-Lezer, Bourg-la-Reine (FR)

(73) Assignee: L'Oreal, Paris (FR)

( * ) Notice: Subject to any disclaimer, the term of this patent is extended or adjusted under 35 U.S.C. 154(b) by 160 days.

(21) Appl. No.: 10/203,374

(22) PCT Filed: Dec. 11, 2001

(86) PCT No.: PCT/FR01/03938

§ 371 (c)(1),
(2), (4) Date: Aug. 9, 2002

(87) PCT Pub. No.: WO02/47605

PCT Pub. Date: Jun. 20, 2002

(65) Prior Publication Data

US 2003/0044367 A1 Mar. 6, 2003

(30) Foreign Application Priority Data

Dec. 12, 2000 (FR) .............................. 0016180

(51) Int. Cl.
*G01J 3/46* (2006.01)
*A61K 7/00* (2006.01)

(52) U.S. Cl. .................. 356/402; 356/432; 424/401

(58) Field of Classification Search ................ 356/402, 356/408–409, 425, 432–434; 424/401, 61, 424/63, 64, 69, 70.7; 436/8, 46, 173
See application file for complete search history.

(56) References Cited

U.S. PATENT DOCUMENTS 4,885,709 A * 12/1989 Edgar et al. .................. 702/30
5,972,359 A 10/1999 Sine et al. .................. 424/401

FOREIGN PATENT DOCUMENTS

JP 08 225316 9/1996
JP 11 106216 4/1999

* cited by examiner

Primary Examiner—Gregory J. Toatley, Jr.
Assistant Examiner—Roy M. Punnoose
(74) Attorney, Agent, or Firm—Finnegan, Henderson, Farabow, Garrett & Dunner, L.L.P.

(57) ABSTRACT

The invention relates to a process for the manufacture of a colored make-up cosmetic composition which makes it possible to produce a transparent or translucent colored coat on the skin, lips or superficial body growths, comprising the following successive steps:
(1) selecting a cosmetically acceptable base having bulk opaqueness, translucency or transparency,
(2) preparing at least one series of samples of this cosmetic base, each series comprising increasing amounts of a coloring agent dissolved or dispersed in the cosmetically acceptable base,
(3) spreading each of the samples of the one or more series over a transparent slide having a recess with a depth of 10 µm,
(4) measuring, for each of the samples of the one or more series, the transmission of the layer thus formed at the wavelength corresponding to the maximum of one of the absorption or scattering peaks ($\lambda_{max}$) of the coloring agent,
(5) drawing a calibration curve by plotting the values of the transmission at $\lambda_{max}$ as a function of the concentration of the coloring agent,
(6) selecting, from the calibration curve thus obtained, a concentration of the coloring agent corresponding to a transmission at $\lambda_{max}$ of between 20% and 80%, and
(7) incorporating at least one coloring agent from at least one series, at the concentration selected in step (6), in a cosmetic base in the liquid state identical to or different from that used in step (1),
and to the cosmetic compositions obtained according to this process.

21 Claims, No Drawings

PROCESS FOR MAKING A COLORED MAKE-UP COSMETIC COMPOSITION WITH CONTROLLED TRANSMITTANCE

The present invention relates to a process for the manufacture of colored make-up cosmetic compositions with controlled transmission and to the compositions obtained by this process.

The contribution of color to the skin, lips and superficial body growths, in particular the hair, nails and eyelashes, has always been an important subject of research in the cosmetics field and very particularly in the field of make-up.

This contribution of color is generally carried out in the form of white or colored pigments, optionally in combination with dyes, in cosmetic bases, giving rise to covering colored coats (lipstick, mascara, eye shadow, eyeliner, nail varnish, foundation) or semitransparent colored coats (foundation, eye shadow, lipstick, nail varnish), the desired effect generally being the production of an intense color or the masking of underlying imperfections.

In the field of foundations, for example, the masking of skin imperfections by covering or semicovering products is, however, virtually always accompanied, despite the application as a very fine layer, by a degree of visibility of the coat and by an unnatural appearance, which is generally undesirable.

Furthermore, there exist cosmetic compositions, such as care creams, which, after application as a fine layer, are entirely transparent or are sufficiently translucent (see WO 98/5234) to retain the natural appearance of the skin and to only lightly mask the imperfections of the latter. However, these products do not make it possible to color the physiological substrate on which they are deposited.

The inventors set a target of developing a novel range of noncovering make-up products which make it possible to deposit a color on the skin, lips or superficial body growths while remaining entirely "invisible", that is to say products capable of giving coats which are sufficient transparent or translucent to retain the natural appearance of the underlying surface.

The manufacture of such make up compositions requires not only the choice of an appropriate cosmetic base but also the determination of the appropriate concentration of coloring agent for the production of a sufficiently colored and transparent or translucent coat.

In point of fact, the transparent or translucent nature and/or the intensity of coloration of a make-up layer are impossible to predict from the appearance of the cosmetic composition. This is because a "bulk" entirely opaque cosmetic composition can give rise to a translucent coat, indeed even an entirely transparent coat.

Until now, a person skilled in the art evaluated the make-up rendering with the naked eye. The results of this observation depend on the illumination and application conditions and on the characteristic color of the substrate. This is reflected by poor reproducibility and the impossibility of transferring the results obtained to all cosmetic substrates.

To overcome the problems set out above, the inventors have developed a process which makes it possible to manufacture, with good reproducibility, colored make-up cosmetic compositions which, independently of their "bulk" degree of opaqueness, give rise to coats simultaneously combining a coloration which is visible to the naked eye and a translucency or transparency which is sufficient to retain the natural appearance of the cosmetic substrate, such as the skin, lips or superficial body growths.

A subject matter of the invention is consequently a process comprising the following successive steps:
(1) selecting a cosmetically acceptable base having bulk opaqueness, translucency or transparency,
(2) preparing at least one series of samples of this cosmetic base, each series comprising increasing amounts of a coloring agent dissolved or dispersed in the cosmetically acceptable base,
(3) spreading each of the samples of the one or more series over a transparent slide having a recess with a depth of 10 μm,
(4) measuring, for each of the samples of the one or more series, the transmission of the layer thus formed at the wavelength corresponding to the maximum of one of the absorption or scattering peaks ($\lambda_{max}$) of the coloring agent,
(5) drawing a calibration curve by plotting the values of the transmission at $\lambda_{max}$ as a function of the concentration of the coloring agent,
(6) selecting, from the calibration curve thus obtained, a concentration of the coloring agent corresponding to a transmission at $\lambda_{max}$ of between 20% and 80%, preferably between 25% and 80%, and
(7) incorporating at least one coloring agent from at least one series, at the concentration selected in step (6), in a cosmetic base in the liquid state identical to or different from that used in step (1).

Another subject matter of the invention is a colored make-up cosmetic composition with controlled transmission prepared according to the above process.

In the present application, the degree of transparency or of translucency of the cosmetic bases and of the colored cosmetic compositions is evaluated or described either in "bulk" form or in the form of "make-up rendering". The expression "bulk" refers to the appearance of the base or of the composition as it is provided, for example in a conventional container, and in particular having a thickness of approximately 1 cm. The expression "make-up rendering" denotes the appearance of a layer of cosmetic composition or of cosmetic base having a thickness closer to that of a true make-up coat and in particular a thickness of 10 μm.

The cosmetic bases which can be used in the process of the present invention can be chosen from any cosmetically acceptable base, whether it displays "bulk" opaqueness, transparency or translucency.

The cosmetic bases which can be used according to the invention are preferably substantially colorless.

The cosmetic bases which can be used according to the invention can be hydrophilic or lipophilic phases with a liquid, thickened, gelled, pasty or solid consistency.

Preferably, the base of the composition is in the form of an aqueous or oily gel which is more or less rigid. More especially, this gel is a rigid gel presented in a dish or as a stick, preferably as a stick, and in the anhydrous form. In particular, this base is an anhydrous foundation or lipstick base.

The oily base comprises a fatty phase which is liquid at ambient temperature, such as those used conventionally in cosmetics. This fatty phase can comprise polar oils and/or nonpolar oils.

In particular, the polar oils of the invention are:
(1) hydrocarbonaceous vegetable oils with a high content of triglycerides composed of esters of fatty acids and of glycerol, the fatty acids of which can have various $C_4$ to $C_{24}$ chain lengths, it being possible for these chains to be linear or branched and saturated or unsaturated; these oils are in particular wheat germ, maize, sunflower, karite, castor, sweet almond, macadamia, apricot, soybean, cottonseed, alfalfa, poppy, pumpkinseed, sesame, cucumber, rapeseed, avocado, hazelnut, grape seed, blackcurrant seed, evening primrose, millet, barley, quinoa, olive, rye, safflower, candlenut, passionflower or musk rose oil; or triglycerides of caprylic/capric acid, such as those sold by Stearineries Dubois or those sold under the names Miglyol 810, 812 and 818 by Dynamit Nobel;

(2) synthetic oils or synthetic esters of formula $R_aCOOR_b$ in which $R_a$ represents the residue of a linear or branched fatty acid comprising from 1 to 40 carbon atoms and $R_b$ represents a hydrocarbonaceous chain, in particular a branched hydrocarbonaceous chain, comprising from 1 to 40 carbon atoms, provided that $R_a+R_b$ is $\geq 10$, such as, for example, purcellin oil (cetostearyl octanoate), isononyl isononanoate, $C_{12}$ to $C_{15}$ alkyl benzoate, isopropyl myristate, 2-ethyhexyl palmitate, isostearyl isostearate, or octanoates, decanoates or ricinoleates of alcohols or of polyalcohols; hydroxylated esters, such as isostearyl lactate or diisostearyl malate; and pentaerythritol esters;

(3) synthetic ethers having from 10 to 40 carbon atoms;
(4) $C_8$ to $C_{26}$ fatty alcohols, such as oleyl alcohol;
(5) $C_8$ to $C_{26}$ fatty acids, such as oleic acid, linolenic acid and linoleic acid; and
(6) mixtures thereof.

The nonpolar oils according to the invention are in particular silicone oils, such as volatile or nonvolatile and linear or cyclic polydimethylsiloxanes (PDMS) which are liquid at ambient temperature; polydimethylsiloxanes comprising alkyl or alkoxy side groups and/or alkyl or alkoxy groups at the chain end, which groups each have from 2 to 24 carbon atoms; phenylated silicones, such as phenyl trimethicones, phenyl dimethicones, phenyltrimethylsiloxydiphenylsiloxanes, diphenyl dimethicones, diphenylmethyldiphenyltrisiloxanes or (2-phenylethyl)trimethylsiloxysilicates; volatile or nonvolatile and linear or branched hydrocarbons of synthetic or mineral origin, such as volatile liquid paraffins (isoparaffins, such as isododecane) or nonvolatile liquid paraffins, and their derivatives, liquid petrolatum, liquid lanolin, polydecenes, hydrogenated polyisobutene, such as parleam oil, squalane or arara oil; and their mixtures.

The oils are preferably nonpolar oils and more especially an oil or a mixture of oils of the hydrocarbonaceous type of mineral or synthetic origin chosen in particular from alkanes, such as parleam oil, isoparaffins, such as isododecane, squalane and their mixtures. These oils are advantageously used in combination with one or more phenylated silicone oils.

The liquid fatty phase preferably comprises at least one nonvolatile oil chosen in particular from hydrocarbonaceous oils of mineral, vegetable or synthetic origin, synthetic esters or ethers, silicone oils and their mixtures.

The total liquid fatty phase represents, in practice, from 5 to 99.95% of the total weight of the composition, preferably from 10 to 80%, and more particularly from 20 to 75%, of the total weight of the composition.

This fatty phase is advantageously structured by a gelling agent for fatty phases, such as
(1) gelling polyamides, in particular with a molecular mass of less than 100 000, and preferably less than 50 000, for example with a molecular mass ranging from 2 000 to 20 000, optionally comprising alkyl side groups or alkyl groups at the chain end having from 8 to 120 carbon atoms, and preferably from 12 to 60 carbon atoms,
(2) hydrophobic galactomannans comprising in particular from 1 to 6, and preferably from 2 to 4, OH groups per monosaccharide unit which are substituted by a $C_{1-6}$, preferably $C_{1-3}$, alkyl group,
(3) hydrophobic pyrogenic silicas,
(4) waxes,
(5) modified clays,
(6) and the combinations of these gelling agents.

The gelling polyamides are, for example, the polyamide resins resulting from the condensation of an aliphatic dicarboxylic acid and of a diamine, including the compounds having more than 2 carboxyl groups and more than 2 amine groups, the carboxyl and amine groups of adjacent individual units being condensed by an amide bond. These polyamide resins are in particular those sold under the Versamid® trademark by General Mills Inc. and Henkel Corp. (Versamid® 930, 744 or 1655) or by Olin Mathieson Chemical Corp. under the Onamid® trademark, in particular Onamid® S or C. These resins have a weight-average molecular mass ranging from 6 000 to 9 000. For further information on these polyamides, reference maybe made to U.S. Pat. Nos. 3,645,705 and 3,148,125. More specifically, use is made of Versamid® 930 or 744.

Use may also be made of the polyamides sold by Arizona Chemical under the Uni-Rez references (2658, 2931, 2970, 2621, 2613, 2624, 2665, 1554, 2623, 2662) and the product sold under the reference Macromelt 6212 by Henkel. For further information on these polyamides, reference may be made to U.S. Pat. No. 5,500,209.

The polyamides can also be those resulting from a polycondensation between a carboxylic diacid comprising at least 32 carbon atoms (in particular from 32 to 44 carbon atoms) and a diamine having at least 2 carbon atoms (in particular from 2 to 36 carbon atoms). The diacid is preferably a dimer of a fatty acid having at least 16 carbon atoms, such as oleic, linoleic or linolenic acid. The diamine is preferably ethylenediamine, hexylenediamine or hexamethylenediamine. If the polymers comprise one or two end carboxylic acid groups, it is advantageous to esterify them with a monoalcohol having at least 4 carbon atoms, preferably from 10 to 36 carbon atoms, more preferably from 12 to 24 carbon atoms, and still more preferably from 16 to 24 carbon atoms, for example, 18 carbon atoms.

These polymers are more especially those disclosed in U.S. Pat. No. 5,783,657 of Union Camp. Each of these polymers satisfies in particular the following formula (I):

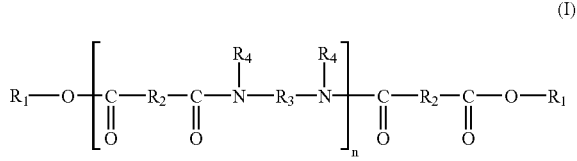

(I)

in which n denotes a whole number of amide units such that the number of ester groups represents from 10% to 50% of the total number of the ester and amide groups; each of the $R_1$ symbols independently denotes an alkyl or alkenyl group having at least 4 carbon atoms and in particular from 4 to 24 carbon atoms; each of the $R_2$ symbols independently represents a $C_4$ to $C_{42}$ hydrocarbonaceous group, provided that 50% of the $R_2$ groups represent a $C_{30}$ to $C_{42}$ hydrocarbonaceous group; each of the $R_3$ symbols independently represents an organic group provided with at least 2 carbon atoms, with hydrogen atoms and optionally with one or more oxygen or nitrogen atoms; and each of the $R_4$ symbols independently represents a hydrogen atom, a $C_1$ to $C_{10}$ alkyl group or a direct bond to $R_3$ or to another $R_4$, so that the nitrogen atom to which both $R_3$ and $R_4$ are bonded forms part of a heterocyclic structure defined by $R_4$—N—$R_3$, with at least 50% of the $R_4$ groups representing a hydrogen atom.

In the specific case of the formula (I), the optionally functionalized end fatty chains within the meaning of the invention are end chains bonded to the final heteroatom, in this instance nitrogen, of the polyamide backbone.

In particular, the ester groups of the formula (I), which form part of the end and/or side fatty chains within the meaning of the invention, represent from 15 to 40% of the total number of the ester and amide groups, and more preferably from 20 to 35%. Furthermore, n advantageously represents an integer ranging from 1 to 5, and preferably of greater than 2.

Preferably, $R_1$ is a $C_{12}$ to $C_{22}$ alkyl group and more preferably a $C_{16}$ to $C_{22}$ alkyl group. Advantageously, $R_2$ can be a $C_{10}$ to $C_{42}$ hydrocarbonaceous (alkylene) group. Preferably, at least 50%, and more preferably at least 75%, of the $R_2$ symbols are groups having from 30 to 42 carbon atoms. The other $R_2$ symbols are $C_4$ to $C_{19}$ and even $C_4$ to $C_{12}$ hydrogenated groups. Preferably, $R_3$ represents a $C_2$ to $C_{36}$ hydrocarbonaceous group or a polyoxyalkylene group and $R_4$ represents a hydrogen atom. More preferably, $R_3$ represents a $C_2$ to $C_{12}$ hydrocarbonaceous group.

The hydrocarbonaceous groups can be linear, cyclic or branched and saturated or unsaturated groups. Furthermore, the alkyl and alkylene groups can be linear or branched and saturated or unsaturated groups.

According to the invention, the structuring of the liquid fatty phase is preferably obtained using one or more polymers of formula (I). In general, the polymers of formula (I) are provided in the form of blends of polymers, it being possible for these blends to additionally comprise a synthetic product corresponding to a compound of formula (I) where n has the value 0, that is to say a diester.

These polymers, because of their fatty chain(s), exhibit good solubility in oils and thus result in macroscopically homogeneous compositions, even with a high (at least 25%) level of polymer, in contrast to polymers devoid of a fatty chain.

Mention may be made, as preferred structuring polymers of formula (I) which can be used in the invention, of the polyamides modified by side fatty chains and/or end fatty chains having from 8 to 120 carbon atoms, and in particular from 12 to 68 carbon atoms, the end fatty chains being bonded to the polyamide backbone via ester groups. These polymers preferably comprise a fatty chain at each end of the polymer backbone and in particular of the polyamide backbone.

Mention may be made, as examples of structuring polyamides of formula (I) which can be used in the composition according to the invention, of the commercial products sold by Arizona Chemical under the names Uniclear® 80 and Uniclear® 100. They are sold respectively in the form of an 80% (as active material) gel in a mineral oil and of a 100% (as active material) gel. They have a softening point of 88 to 94° C. These commercial products are a blend of copolymers of a $C_{36}$ diacid condensed with ethylenediamine, with a weight-average molecular mass respectively of approximately 600 or 4 000). The end ester groups result from the esterification of the remaining acid endings with cetyl alcohol or stearyl alcohol or their mixtures (also known as cetearyl alcohol).

The galactomannans are in particular ethylated guar derivatives having especially a degree of substitution of 2 to 3, such as those sold by Aqualon under the names N-Hance-AG-200® or N-Hance-AG-50®.

The pyrogenic silica preferably exhibits a particle size which can be nanometric to micrometric, for example ranging from approximately from 5 to 200 nm.

Pyrogenic silicas can be obtained by high temperature hydrolysis of a volatile silicon compound in an oxyhydrogen flame, producing a finely divided silica. This process makes it possible in particular to obtain hydrophilic silicas which exhibit a large number of silanol groups at their surfaces. Such hydrophilic silicas are, for example, sold under the names Aerosil 130®, Aerosil 200®, Aerosil 255®, Aerosil 300® and Aerosil 380® by Degussa or under the names Cab-O-Sil HS-5®, Cab-O-Sil EH-5®, Cab-O-Sil LM-130®, Cab-O-Sil MS-55® and Cab-O-Sil M-5® by Cabot.

It is possible to chemically modify the surface of said silica by a chemical reaction which reduces the number of silanol groups. It is possible in particular to substitute silanol groups by hydrophobic groups and thus to obtain a hydrophobic silica. The hydrophobic groups can be:
(1) trimethylsiloxy groups, which are obtained in particular by treatment of pyrogenic silica in the presence of hexamethyldisilazane and are named "Silica silylate" according to the CTFA (6th edition, 1995); they are sold, for example, under the name Aerosil R812® by Degussa and under the name Cab-O-Sil TS-530® by Cabot;
(2) dimethylsilyloxy or polydimethylsiloxane groups, which are obtained in particular by treatment of pyrogenic silica in the presence of polydimethylsiloxane or of dimethyldichlorosilane and are named "Silica dimethyl silylate" according to the CTFA (6th edition, 1995); they are sold, for example, under the names Aerosil R972® and Aerosil R974® by Degussa and under the names Cab-O-Sil TS-610® and Cab-O-Sil TS-720® by Cabot; and
(3) groups resulting from the reaction of the pyrogenic silica with alkoxysilanes or siloxanes; these treated silicas are, for example, those sold under the reference Aerosil R805® by Degussa.

Waxes are crystalline fatty compounds which are solid at ambient temperature (25° C.) and which have a melting point of greater than 45° C.

Mention may be made, as waxes which can be used in the invention, of hydrocarbonaceous, silicone and/or fluorinated waxes optionally comprising ester or hydroxyl functional groups. Mention may be made, by way of examples, of beeswax, which is optionally modified, carnauba or candelilla wax, ouricury wax, Japan wax, montan wax, paraffin wax, lignite or microcrystalline waxes, sugarcane or cork fiber waxes, ceresin or ozokerite; synthetic waxes, such as polyethylene waxes resulting from the polymerization or copolymerization of ethylene, silicone waxes, such as alkyl or alkoxy dimethicones having from 10 to 45 carbon atoms, poly(di)methylsiloxane esters, the ester chain of which comprises at least 10 carbon atoms, Fischer-Tropsch waxes, hydrogenated oils, such as hydrogenated castor oil or hydrogenated jojoba oil, certain fatty acids, such as stearic, myristic or behenic acid, and their mixtures.

The waxes can be provided in the form of stable dispersions of colloidal wax particles which can be prepared according to known methods, such as those described in "Microemulsions Theory and Practice", edited by L. M. Prince, Academic Press (1977), pages 21–32.

Mention may be made, as examples of modified clays which can be used as structuring agents, of hectorites modified by a $C_{10-22}$ fatty acid ammonium chloride, such as the hectorite modified by distearyldimethylammonium chloride sold under the name Bentone® 34 or Bentone® 38 by Rheox.

The base can also comprise pasty fatty substances which are solid at ambient temperature but which have a melting point lower than that of waxes.

Mention may be made, as pasty fatty substances, of fatty substances having a melting point ranging from 20 to 55° C., and preferably from 25 to 45° C., and/or a viscosity at 40° C. ranging from 0.1 to 40 Pa·s, and more preferably from 0.5 to 25 Pa·s, measured with a Contraves TV equipped with an MS-r3 or Ms-r4 rotor rotating at 60 Hz. Mention may be made, as examples of pasty fatty substances, of PDMSs having side chains of the alkyl or alkoxy type comprising from 8 to 24 carbon atoms, such as stearyl dimethicone; esters of fatty alcohols or of fatty acids, such as cholesterol esters, poly(vinyl laurate) or arachidyl propionate; and lanolins and their derivatives, such as acetylated lanolins, isopropyl lanolate or oxypropylenated lanolins.

When the gel is an aqueous gel, use may be made of any gelling agent for aqueous phases of the cellulose derivative type, such as hydroxyethylcellulose and carboxymethylcellulose, or acrylic derivative type, such as crosslinked copolymers of acrylic acid and of $C_{10-30}$ alkyl acrylates, for example the Pemulen® series and Carbopol® 980, which are sold by Goodrich, clay derivatives of the sodium magnesium silicate type, such as Laponite XLS or XLG, sold by Laporte, and the combinations of these gelling agents. The aqueous gel can be a water-based gel or a gel based on a water/alcohol mixture.

The gelling agent represents from 0.05 to 90% by weight, preferably from 2 to 60% by weight, and more preferably from 5 to 40% by weight, of the total weight of the cosmetic composition.

According to the process of the present invention, increasing amounts of at least one coloring agent are introduced into the cosmetic bases described above.

According to the present invention, the term "coloring agent" encompasses in particular water-soluble or fat-soluble dyes, pigments, pearlescence agents, lakes and their mixtures.

Mention may be made, as water-soluble dyes, of synthetic dyes, such as fuchsin, plant extracts, such as extracts of sorghum, of *Pterocarpus soyauxii*, of *Monascus*, of *Lawsonia inermis*, of *Mercurialis perenis*, of *Helianthus aanus*, of *Impatiens balsamina*, of *Curcuma longa*, of *Phytolacca decandra*, of *Solidago aureus*, of *Juglans regia*, of *Iris germanica*, of *Alkanna tinctoria*, of *Chrozophoro tinctoria* or of *Isatis tinctoria*, and the mixtures of these dyes.

The fat-soluble dyes are, for example, Sudan red III (CTFA: D&C Red 17), lutein, quinizarin green (CTFA: D&C Green 6), alizurol purple SS (CTFA: D&C Violet No. 2), carotenoid derivatives, such as lycopene, β-carotene, bixin or capsantein, annatto and fuchsin derivatives (see Example 2), and their mixtures.

A number of these dyes, such as extracts of *Pterocarpus soyauxii, Monascus* and *Lawsonia inermis*, have a strong affinity for the skin and can thus confer a semipermanent coloring thereon, that is to say a coloring which withstands being washed several times.

The term "pigments" should be understood as meaning white or colored, inorganic or organic and coated or uncoated particles. Mention may be made, for example, of titanium dioxide, zirconium dioxide, cerium dioxide, zinc oxide, iron oxide, chromium oxide, ferric blue, chromium hydrate, carbon black, ultramarines (polysulfides of aluminum silicates), manganese violet, manganese pyrophosphate and some metal powders, such as silver or aluminum powders, and their mixtures.

The term "pearlescence agents" is understood to mean white nacreous pigments, such as mica covered with titanium oxide or with bromuth oxychloride, and colored nacreous pigments, such as titanium oxide-coated mica covered with iron oxides, ferric blue or chromium oxide or with a precipitated typical organic pigment.

The lakes which can be used in the compositions of the present invention are, for example, lakes based on cochineal carmine or based on calcium, barium, aluminum, strontium or zirconium salts, on acid dyes, and their mixtures.

Each of the samples obtained by incorporation of increasing amounts of a coloring agent is spread over a specific sample carrier.

It is a transparent slide, the size of which depends on the measuring cell of the spectrophotometer used (20 mm×10 mm×3 mm for a Cary 300), having at its surface a flat recess with a depth of 10 μm. This flat recess is filled with the sample and the excess is optionally leveled down, so as to obtain a perfectly even and reproducible layer with a thickness of 10 μm, in particular in the case of a sample with a thickened, gelled, pasty or solid consistency.

The transparent slide can be composed of any material which does not absorb or reflect visible light in the wavelength region studied, such as, for example, glass or quartz. The transparent slide used for the transmission measurements of the process of the present invention is preferably made of quartz.

The layer thickness of 10 μm at which the measurements of transmission of the compositions of the present invention are carried out was chosen because it corresponds substantially to the thickness of a make-up coat obtained, for example, with a foundation or a lipstick. The values obtained by these measurements therefore give a good description of the make-up rendering, that is to say of the immediate visual impression which the make-up layer gives.

The transmission as defined here is equal to the ratio of the intensity of light transmitted by the sample ($I_t$) to the intensity of light transmitted by the control ($I_0$), expressed as %:

$$T(\%)=I_t/I_0$$

The measurements are carried out using a double-beam UV/visible spectrophotometer, Cary 300 model from Varian, in transmission mode and by using, as control, a transparent slide with an identical thickness to that receiving the sample.

As indicated above, the transmission of each sample is measured at the wavelength corresponding to the maximum ($\lambda_{max}$) of one of the absorption peaks (dye) or scattering peaks (pigment) of the coloring agent in the visible light region ($\lambda$=400 to 750 nm).

The error in the measurement of the transmission is ±5%.

A calibration curve is subsequently drawn by plotting the values of the transmission at $\lambda_{max}$ as a function of the concentration of the coloring agent.

The calibration curve thus obtained makes it possible subsequently to discover, simply by reading, the range of concentrations of the coloring agent which gives cosmetic coats with a thickness of 10 μm having a transmission of between 20% and 80%, and preferably between 25% and 80%. This is because the inventors have found that this transmission range corresponds to cosmetic coats having the desired properties, that is to say a coloration visible to the naked eye and a transparency or translucency which is sufficient to retain the natural appearance of the underlying substrate.

For a mixture of coloring agents, the above calibration curve has to be produced for each of the coloring agents.

The final step (7) of the process for the manufacture of cosmetic compositions according to the invention comprises the incorporation, in a cosmetic base, of at least one coloring agent in the appropriate concentrations determined in the manner described above.

To receive the coloring agent, the cosmetic base must, of course, be in the liquid state. The liquid consistency can be a property of the base as such at ambient temperature or it can be the result of the melting or dissolution of a cosmetic base which is solid at ambient temperature.

The solid anhydrous cosmetic bases preferred according to the present invention are preferably liquefied by melting at a temperature slightly above their melting point.

The invention is illustrated by the following examples of cosmetic compositions prepared according to the process of the invention:

EXAMPLE 1

| Anhydrous lipstick with an opaque base | |
|---|---|
| Oxypropylenated beeswax | 14.5% |
| Microcrystalline wax | 3% |
| Oxypropylenated lanolin wax | 2% |
| Sesame oil | 10% |
| Arara oil | 18% |
| Lanolin | 20% |
| Acetylated lanolin | 6% |
| MMB Red 33/3 complex[1] | 0.2% |
| | (coloring active material) |
| Oleyl erucate | q.s. for 100% |

All the percentages are understood to be by weight.

MMB Red 33/3 complex, sold by Phytocos and denoting the mixture: disodium salt of fuchsin acid d/lysine palmitate-myristate/dipropylene glycol/benzoic acid/phenoxyethanol/3% solution of D&C Red No. 33 (CI: 17200)/preservatives: methyl, butyl, ethyl, propyl p-hydroxybenzoate.

The waxes and the oils are introduced into a casserole and the mixture is heated as far as the melting temperature of the wax having the highest melting temperature. The mixture is then placed at 10° C. above this temperature. The dye is introduced into the mixture and the combined contents are homogenized with magnetic stirring for 1 hour. The composition is cast in a mold heated at 45° C. to form a stick which is placed, after solidification has begun, in a freezer for 15 minutes (−21° C.).

The transmission at 530 nm ($\lambda_{max}$ of the dye) of a coat with a thickness of 10 μm of the above lipstick composition is 29%. This lipstick has a bulk opaque appearance and gives a transparent cosmetic coat which confers a fuchsia pink color on the lips. The color deposited is very intense.

EXAMPLE 2

| Anhydrous lipstick with a transparent base | |
|---|---|
| Uniclear ® 100 | 25% |
| Octyldodecanol | 10% |
| MMB Red ® 33/3 complex | 0.2% |
| | (coloring active material) |
| Parleam oil | q.s. for 100% by weight |

Uniclear® 100: condensate of a hydrogenated $C_{36}$ diacid and ethylenediamine esterified with stearyl alcohol (weight-average molar mass approximately 4 000), sold by Arizona Chemical.

MMB Red 33/3 complex, sold by Phytocos and denoting the mixture: disodium salt of fuchsin acid d/lysine palmitate-myristate/dipropylene glycol/benzoic acid/phenoxyethanol/3% solution of D&C Red No. 33 (CI: 17200)/preservatives: methyl, butyl, ethyl, propyl p-hydroxybenzoate.

The Uniclear® 100 and the oils are introduced into a casserole. The combined contents are stirred magnetically and are heated in a first step to 100° C. to bring the Uniclear to the liquid state. Heating is then continued as far as the temperature necessary to produce a homogeneous transparent liquid. The mixture is then placed at 10° C. above this temperature. The dye is introduced into the mixture and the combined contents are homogenized with magnetic stirring for 1 hour. The composition is cast in a mold heated at 45° C. to form a stick which is placed, after solidification has begun, in a freezer for 15 minutes (−21° C.).

The composition obtained has a bulk translucent appearance (1 cm) and gives rise to a completely transparent coat with a fuchsia pink color having a transmission at 530 nm ($\lambda_{max}$ of the dye) and having a thickness of 10 μm of 40%.

What is claimed is:

1. A process for making a colored make-up cosmetic composition which produces a transparent of translucent colored coat on at least one of the skin, lips and superficial body growths, comprising the following successive steps:
   (1) selecting a cosmetically acceptable base having at least one of bulk opaqueness, translucency and transparency,
   (2) preparing at least one series of samples of the cosmetic base, each series comprising increasing amounts of a coloring agent dissolved or dispersed in the cosmetically acceptable base,
   (3) spreading each of the samples of the at least one series over a transparent slide having a recess with a depth of 10 μm,
   (4) measuring, for each of the samples of the at least one series, the transmission of the layer thus formed at a wavelength corresponding to the maximum of the absorption or scattering peak ($\lambda_{max}$) of the coloring agent,
   (5) drawing a calibration curve by plotting the values of the transmission at $\lambda_{max}$ as a function of the concentration of the coloring agent,
   (6) selecting, from the calibration curve thus obtained, a concentration of the coloring agent corresponding to a transmission at $\lambda_{max}$ ranging from 20% to 80%, and
   (7) incorporating the at least one coloring agent from the at least one series, at the concentration selected in step (6), in a cosmetic base in the liquid state and identical to or different from that used in step (1).

2. The process according to claim 1, wherein, in step (6), the concentration of the coloring agent corresponding to a transmission at $\lambda_{max}$ ranging from 25% to 80% is selected from the calibration curve.

3. The process according to claim 1, wherein the cosmetically acceptable base is a substantially colorless base.

4. The process according to claim 1, wherein the cosmetically acceptable base is chosen from aqueous gels and oily gels.

5. The process according to claim 4, wherein the gel is in stick form.

6. The process according to claim 1, wherein the cosmetically acceptable base is an anhydrous gel formed from a fatty phase which is liquid at ambient temperature comprising an oil chosen from polar oils and nonpolar oils, wherein the fatty phase is structured by a gelling agent for fatty phases which is chosen from at least one of hydrophobic pyrogenic silicas, gelling polyamides, hydrophobic galactomannans, waxes, and modified clays.

7. The process according to claim 6, wherein the gelling polyamide corresponds to the formula (I):

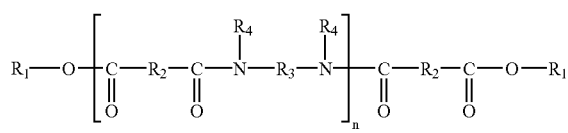
(I)

in which n represents a whole number such that the number of ester groups ranges from 10% to 50% of the total number of the ester and amide groups;

$R_1$, which may be identical or different, represents a group chosen from alkyls having at least 4 carbon atoms and alkenyls having at least 4 carbon atoms;

$R_2$, which may be identical or different, represents a $C_4$ to $C_{42}$ hydrocarbonaceous group, provided that 50% of the $R_2$ groups represent a $C_{30}$ to $C_{42}$ hydrocarbonaceous group;

$R_3$, which may be identical or different, represents an organic group having at least 2 carbon atoms, hydrogen atoms, and optionally at least one atom chosen from oxygen atoms and nitrogen atoms; and $R_4$, which may be identical or different, represents a group chosen from hydrogen atoms, $C_1$ to $C_{10}$ alkyls, optionally directly bonded to $R_3$ or to another $R_4$, so that the nitrogen atom to which both $R_3$ and $R_4$ are bonded forms part of a heterocyclic structure defined by $R_4$—N—$R_3$, with at least 50% of the $R_4$ groups representing a hydrogen atom.

8. The process according to claim 7, wherein each $R_1$, which may be identical or different, is chosen from alkyls having 4 to 24 carbon atoms and alkenyls having 4 to 24 carbon atoms.

9. The process according to claim 6, wherein the modified clay is a hectorite modified by a $C_{12}$–$C_{22}$ fatty acid ammonium chloride.

10. The process according to claim 1, wherein the coloring agent is chosen from at least one of water-soluble dyes, fat soluble dyes, pigments, pearlescence agents, and lakes.

11. The process according to claim 10, wherein the water-soluble dye is chosen from at least one of fuchsin, extracts of sorghum, *Pterocarpus soyauxii, Monascus, Lawsonia inermis, Mercurialis perenis, Helianthus aanus, Impatiens balsamina, Curcuma longa, Phytolacca decandra, Solidago aureus, Juglans regia, Iris germanica, Alkanna tinctoria, Chrozophoro tinctoria*, and *Isatis tinctoria*.

12. The process according to claim 10, wherein the fat-soluble dye is chosen from at least one of Sudan red III, lutein, quinizarin green, alizural purple SS, carotenoid derivatives, annatto derivatives, and fuchsin derivatives.

13. The process according to claim 12, wherein the carotenoid derivative is chosen from lycopene, β-carotene, bixin, and capsantein.

14. The process according to claim 10, wherein the pigment is chosen from at least one of white inorganic pigments, colored inorganic pigments, white coated inorganic pigments, white organic pigments, colored coated inorganic pigments, and colored organic pigments.

15. The process according to claim 14, wherein the pigment is chosen from at least one of titanium dioxide, zirconium dioxide, cerium dioxide, zinc oxide, iron oxide, chromium oxide, ferric blue, chromium hydrate, carbon black, ultramarines, manganese violet, manganese pyrophosphate, and metal powders.

16. The process according to claim 15, wherein the metal powder is chosen from silver powders and aluminum powders.

17. The process according to claim 10, wherein the pearlescence agent is chosen from mica covered with at least one of titanium oxide and bismuth oxychloride and titanium oxide-coated mica covered with at least one of iron oxide, ferric blue, chromium oxide, and precipitated organic pigments.

18. The process according to claim 10, wherein the lake is chosen from at least one of lakes based on cochineal carmine, lakes based on at least one of calcium salts, barium salts, aluminum salts, strontium salts, and zirconium salts, and lakes based on acid dyes.

19. The process according to claim 1, wherein the process comprises, between steps (3) and (4), an additional step comprising leveling the excess of the sample so as to obtain a layer with a homogenous thickness of 10 μm.

20. The process according to claim 1, wherein the transparent slide is a quartz slide.

21. A colored make-up cosmetic composition with controlled transmission prepared according to a process comprising the following successive steps:

(1) selecting a cosmetically acceptable base having at least one of bulk opaqueness, translucency and transparency, (2) preparing at least one series of samples of the cosmetic base, each series comprising increasing amounts of a coloring agent dissolved or dispersed in the cosmetically acceptable base, (3) spreading each of the samples of the at least one series over a transparent slide having a recess with a depth of 10 μm, (4) measuring, for each of the samples of the at least one series, the transmission of the layer thus formed at a wavelength corresponding to the maximum of the absorption or scattering peak ($\lambda_{max}$) of the coloring agent, (5) drawing a calibration curve by plotting the values of the transmission at $\lambda_{max}$ as a function of the concentration of the coloring agent, (6) selecting, from the calibration curve thus obtained, a concentration of the coloring agent corresponding to a transmission at $\lambda_{max}$ ranging from 20% to 80%, and (7) incorporating at least one second coloring agent from the at least one series, at the concentration selected in step (6), in a second cosmetic base in a liquid state identical to or different from that used in step (1).

* * * * *